United States Patent
Piche-Radley et al.

(10) Patent No.: US 9,526,602 B1
(45) Date of Patent: Dec. 27, 2016

(54) METHOD OF APPLYING ADHESION BARRIERS

(71) Applicants: Anne Piche-Radley, Creve Coeur, MO (US); Della A. Smith, St. Charles, MO (US); Monica D. Dye, St. Louis, MO (US)

(72) Inventors: Anne Piche-Radley, Creve Coeur, MO (US); Della A. Smith, St. Charles, MO (US); Monica D. Dye, St. Louis, MO (US)

( * ) Notice: Subject to any disclaimer, the term of this patent is extended or adjusted under 35 U.S.C. 154(b) by 0 days.

(21) Appl. No.: 14/216,730

(22) Filed: Mar. 17, 2014

Related U.S. Application Data

(60) Provisional application No. 61/794,063, filed on Mar. 15, 2013.

(51) Int. Cl.
 *A61F 2/00* (2006.01)
 *A61B 17/34* (2006.01)
 *A61B 17/00* (2006.01)

(52) U.S. Cl.
 CPC ....... *A61F 2/0063* (2013.01); *A61B 17/00234* (2013.01); *A61B 17/3468* (2013.01); *A61B 17/3478* (2013.01); *A61F 2002/0072* (2013.01); *A61F 2210/0004* (2013.01)

(58) Field of Classification Search
 CPC ............... A61F 2/0063; A61F 2002/0072
 See application file for complete search history.

(56) References Cited

U.S. PATENT DOCUMENTS

| | | | | |
|---|---|---|---|---|
| 5,527,893 | A * | 6/1996 | Burns | A61K 9/0019 514/53 |
| 7,144,588 | B2 * | 12/2006 | Oray | A61L 27/3604 424/543 |
| 2007/0071798 | A1 * | 3/2007 | Herweck | A61F 2/0059 424/443 |
| 2012/0065649 | A1 * | 3/2012 | Towler | A61F 2/0045 606/151 |
| 2013/0129800 | A1 * | 5/2013 | Giammona | A61L 27/20 424/400 |

* cited by examiner

*Primary Examiner* — Howie Matthews
(74) *Attorney, Agent, or Firm* — Harness, Dickey & Pierce, P.L.C.

(57) ABSTRACT

A process for applying an adhesion barrier material to the tissue in a surgical site includes steaming the adhesion barrier material, preferably in a warm environment at a temperature of between about 140° F. (60° C.) and about 170° F. (77° C.); air drying the adhesion barrier material until the surface is not tacky; and applying the adhesion barrier material to tissue at a surgical site.

8 Claims, 3 Drawing Sheets

METHOD OF APPLYING ADHESION BARRIERS

CROSS-REFERENCE TO RELATED APPLICATIONS

This application claims priority to U.S. Provisional Patent Application Ser. No. 61/794,063, filed Mar. 15, 2013. The entire disclosure of the above-referenced application is incorporated herein.

FIELD

The present disclosure relates to adhesion barriers, and in particular to a method of applying adhesion barriers.

BACKGROUND

This section provides background information related to the present disclosure which is not necessarily prior art.

Adhesion barriers, for example SEPRAFILM®, available from Genzyme Corporation, are placed between injured tissues or organs during surgery to separate the tissues and organs while they heal. See, for example, U.S. Pat. No. 5,527,893, the disclosure of which is incorporated herein by reference. These barriers keep the tissues and organs separated until they heal and develop natural protection against the formation of adhesions, and then the film is simply absorbed and eliminated naturally by the body. SEPRAFILM®, products are transparent films that are designed to act as a temporary barrier between tissue layers during the early days of tissue healing, thereby reducing adhesion formation. More specifically, SEPRAFILM® products are sterile bioresorbable transparent adhesion barriers composed of two anionic polysaccharides, namely sodium hyaluronate and carboxymethylcellulose. Together, these two biopolymers are chemically modified with an activating agent 1-(3-dimethylaminopropyl)-3-ethylcarbodimide hydrochloride. SEPRAFILM® products hydrate to a gel within 24 48 hours following placement in the body and then slowly resorb from the abdominal cavity in about five days.

According to the package insert, SEPRAFILM® products are placed at a desired site within the body, with that desired site being as dry as possible. Before placing SEPRAFILM® products in the body, the site of application is thoroughly aspirated of excess fluid. The Seprafilm® products are kept in their package until immediately before use. In one form, for example, the film measures 5 inches by 6 inches, though it can also be cut with scissors to achieve a desired size and shape. When applying, the surgeon should avoid contact with any tissue surfaces until directly at the site of application. The package insert further indicates that if contact does occur, moderate application of standard irrigation solution is used to gently dislodge the film from the unintended tissue surface. Once at the proper site of application, the biomaterial is adhered to the tissue by gently pressing the biomaterial down with a dry glove or instrument. The biomaterial remains at the site of application until it dissolves into a gel. See, e.g., U.S. Pat. No. 7,144,588. During actual usage in the operating room, SEPRAFILM® products are very delicate and cannot be handled directly without risk of crumbling. Surgeons therefore handle it as little as possible. They leave the Seprafilm sandwiched between the enclosed sheets, which do not appear to be radio opaque, while adjusting the Seprafilm sheet onto the tissue. The paper is then removed one at a time to allow the film to adhere to the tissues. If the paper gets too wet or if the film shifts during removal of the paper, the film tends to form into a gel like ball. If the film adheres to unintended tissue, it tears upon removal and must be discarded. In addition, the SEPRAFILM® products must remain relatively flat; it crumbles if attempt is made to roll or fold it to fit down a tr-haf trocar or through a small incision.

The use of adhesion barriers can be challenging because the material is usually brittle and cracks and flakes while being handled. It then becomes difficult for the physician to deliver the adhesion barrier material to the surgical site, and piece together an effective barrier from the bits and pieces of material. The instructions for SEPRAFILM® products specifically instruct that the material be "stored at 2-30° C." SEPRAFILM® products are packed in a Tyvek®1 holder within a plastic sleeve and packed in an outer, sealed, foil pouch. The instructions state when pouch is opened the plastic sleeve should be placed "on a dry, sterile field," and that the membrane should be kept "dry in the holder prior to application."

SUMMARY

This section provides a general summary of the disclosure, and is not a comprehensive disclosure of its full scope or all of its features.

The inventors have discovered that by heating, and preferably steaming the adhesion barrier material in a warm moist environment, and then allowing the material to dry until it is not tacky, the material is not as delicate and difficult to handle and can then be cut to size and applied, or in the case of laparoscopic surgery, folded or rolled for delivery through a trocar. The material can then be assembled into continuous barrier to prevent adhesions between adjacent organs or tissues. If contact is made with unintended tissue, the change in texture allows SEPRAFILM® products to be removed and reapplied while maintaining the integrity of the sheet. Furthermore, the SEPRAFILM® products can be handled directly (without the papers) after this process which decreases the risk of retained foreign bodies within the patient.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 5:
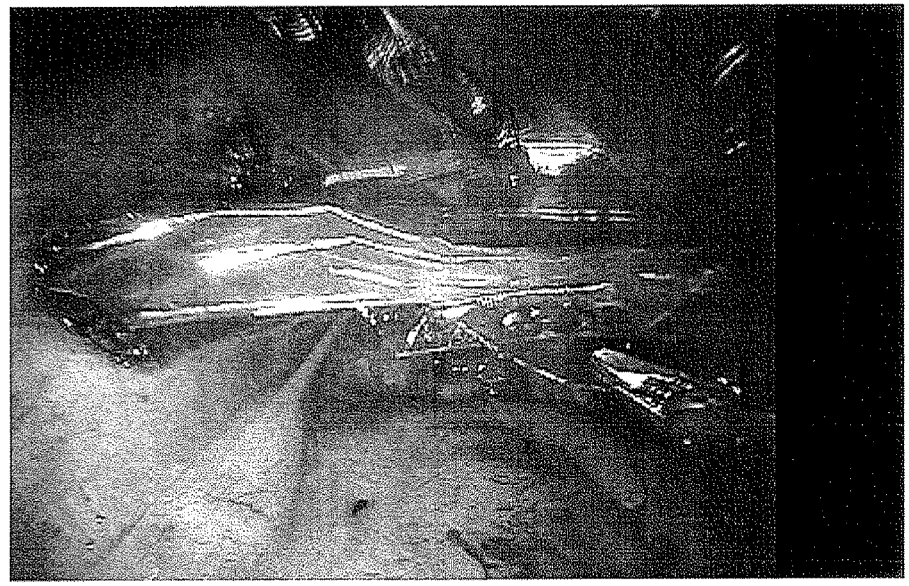
Figure 6:

FIG. 5 is a photograph of a conventional adhesion barrier treated in accordance with the principles of this invention, shown after it has been fanfolded and delivered to a surgical site through a trocar; and FIG. 6 is a photograph of a conventional adhesion barrier treated in accordance with the principles of this invention, shown after it has been fanfolded and delivered to a surgical site through a trocar, and unfolded for application to tissue.

Corresponding reference numerals indicate corresponding parts throughout the several views of the drawings.

DETAILED DESCRIPTION

Example embodiments will now be described more fully with reference to the accompanying drawings.

For descriptive purposes, the elements in the package will be identified as 1) the foil pouch, which is the outer package 2) the inner sleeve, which is open at one end and contains the SEPRAFILM® product 3) the SEPRAFILM® product, sandwiched between two white sheets.

Embodiments of the present invention provide an improved method of preparing and placing adhesions barriers such as SEPRAFILM® barriers. While the preferred embodiment is described with respect to SEPRAFILM® barriers, the invention is not so limited and can be applied to other adhesions barriers.

In accordance with the preferred embodiment, a pouch of the SEPRAFILM® barrier is opened and the inner sleeve is placed in a reclosable container of sterile water or saline at between about 140 and about 170° F. (between about 60 and about 77° C.). The open end of the SEPRAFILM® barrier inner sleeve should be above the level of the water or saline in the container, so that liquid water does not contact the SEPRAFILM® barrier. The SEPRAFILM® barrier should be kept in the closed container to be steamed for approximately five minutes. The inner sleeve of SEPRAFILM® barrier should then be removed from the container, and the SEPRAFILM® barrier should be removed from the inner sleeve. The white sheet should be removed from one side of the SEPRAFILM® barrier, and air dried until it is no longer tacky (usually a minimum of five minutes).

Figure 1:
FIG. 1 is a photograph of a laparoscopic surgical site, showing a conventional, untreated, adhesion barrier delivered through a trocar.
Figure 2:
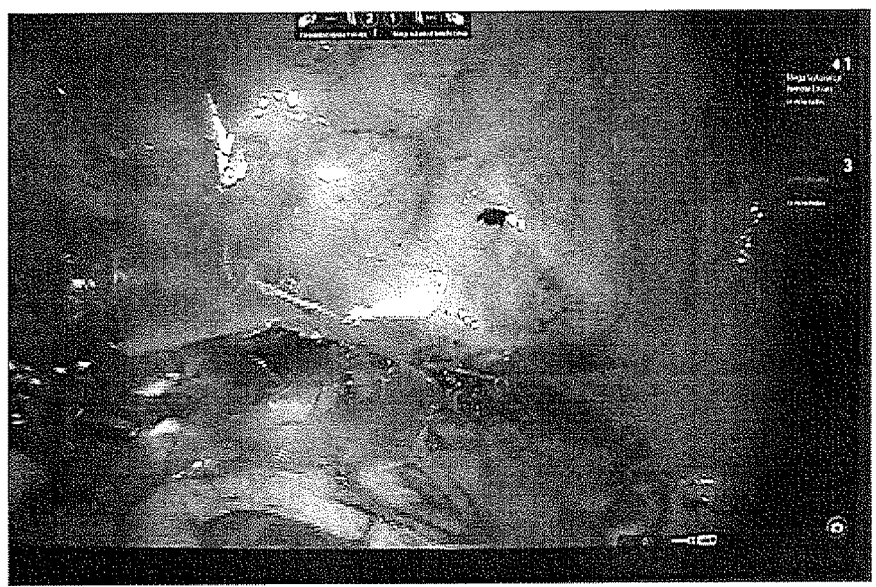
FIG. 2 is a photograph of a laparoscopic surgical site, showing a conventional, untreated, adhesion barrier showing how it breaks up.
Figure 3:
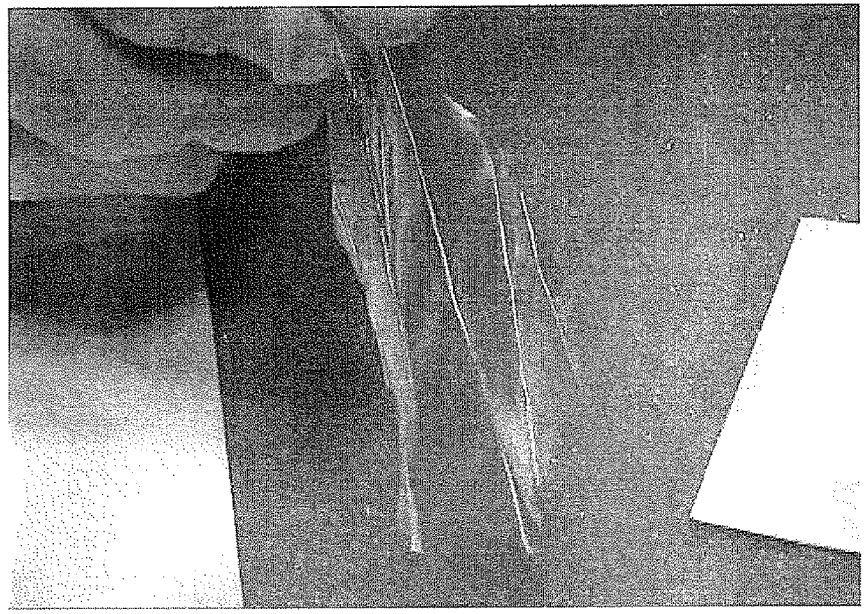
FIG. 3 is a photograph of a conventional adhesion barrier treated in accordance with the principles of this invention, shown as it can be fanfolded in accordance with the principles of this invention.
Figure 4:
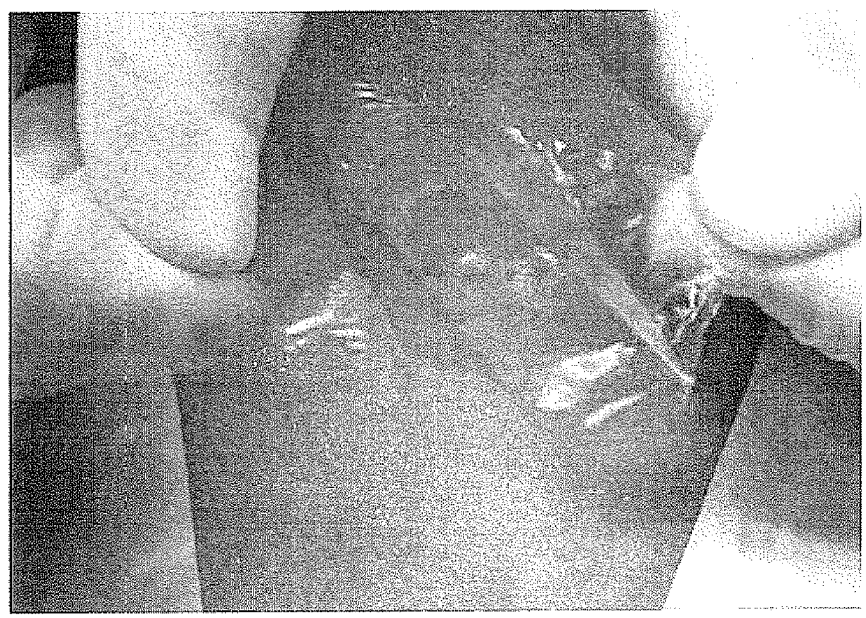
FIG. 4 is a photograph of a conventional adhesion barrier treated in accordance with the principles of this invention, shown as it can be expanded after fanfolding.

The prepared SEPRAFILM® barrier sheet can then be cut the desired size, and placed on the tissue form a barrier, or it can be rolled or folded for delivery through a trocar or surgical opening, and then placed on the tissue to form a barrier. In accordance with the preferred embodiment, the SEPRAFILM® barrier is preferably fan folded so that it can be conveniently transported through the trocar, after which it can be unfolded and applied to the surface of tissues. A square or rectangular segment of the Seprafilm® can be fanfolded along the diagonal (as shown in FIGS. 4-6) or accordion style. Alternatively a square or other shape of the SEPRAFILM® barrier can be rolled to facilitate the delivery through a trocar.

While warm moisture is preferred, five minutes in a cool (room temperature) mist in a closed environment is sufficient.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A process for applying an adhesion barrier material to tissue in a surgical site, comprising:
    steaming a SEPRAFILM® (or equivalent) adhesion barrier material in a warm environment at a temperature of between about 140° F. (60° C.) and about 170° F. (77° C.);
    air drying the adhesion barrier material until the surface is not tacky;
    manipulating the steamed, dried adhesion barrier into the configuration, size and shape necessary to apply to the tissue at a surgical site;
    applying the adhesion barrier material to tissue at the surgical site.

2. The process according to claim 1 wherein the adhesion barrier is air dried for at least five minutes.

3. The process according to claim 1 wherein the adhesion barrier is fan folded.

4. The process according to claim 3 wherein the adhesion barrier is introduced to the surgical site through a trocar.

5. The process according to claim 3 wherein the adhesion barrier is introduced to the surgical site through a surgical opening.

6. The process according to claim 1 wherein the adhesion barrier is rolled.

7. The process according to claim 6 wherein the adhesion barrier is introduced to the surgical site through a trocar.

8. The process according to claim 6 wherein the adhesion barrier is introduced to the surgical site through a surgical opening.

* * * * *